United States Patent [19]

Arison et al.

[11] Patent Number: 4,738,982

[45] Date of Patent: Apr. 19, 1988

[54] HMG-COA REDUCTASE INHIBITORS

[75] Inventors: Byron H. Arison, Watchung, N.J.; Michael D. Greenspan, New York, N.Y.; Joel B. Yudkovitz, Westfield, N.J.

[73] Assignee: Merck & Co., Inc., Rahway, N.Y.

[21] Appl. No.: 856,251

[22] Filed: Apr. 28, 1986

[51] Int. Cl.$^4$ .................. A61K 31/365; C07D 309/30
[52] U.S. Cl. ..................................... 514/460; 549/292; 514/824; 560/256; 424/79
[58] Field of Search .................. 549/292; 514/824, 460

[56] References Cited

U.S. PATENT DOCUMENTS 4,231,938  11/1980  Monaghan et al. ................. 549/292

*Primary Examiner*—Norma S. Milestone
*Attorney, Agent, or Firm*—Joseph F. DiPrima; Michael C. Sudol, Jr.

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) or (II):

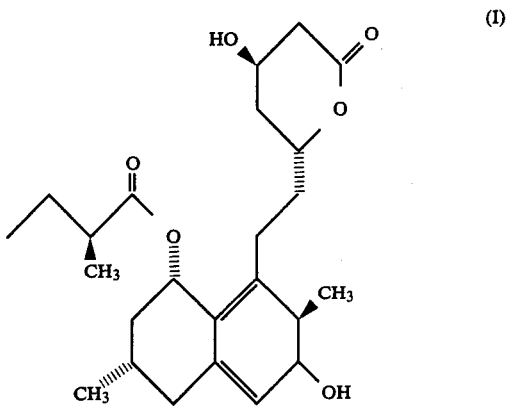

(I)

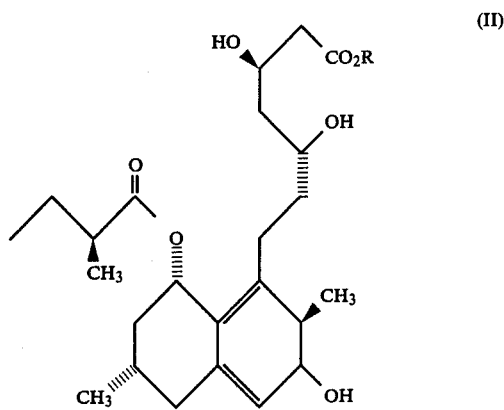

(II)

and pharmaceutically acceptable salts thereof the compounds of the formula (II) in which R is hydrogen are disclosed.

3 Claims, No Drawings

HMG-COA REDUCTASE INHIBITORS

BACKGROUND OF THE INVENTION

Hypercholesterolemia is known to be one of the prime risk factors of cardiovascular disease such as arteriosclerosis, and there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occurring compounds and their semi-synthetic analogs have the following general structural formulae:

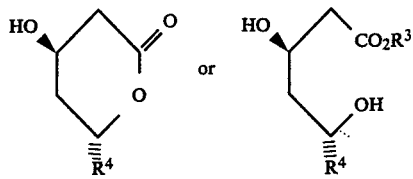

wherein:
$R^3$ is hydrogen, $C_{1-5}$ alkyl or $C_{1-5}$ alkyl substituted with a member of the group consisting of phenyl, dimethylamino, or acetylamino;
$R^4$ is:

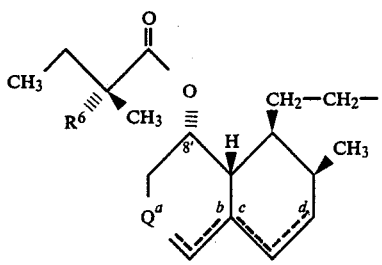

wherein
Q is

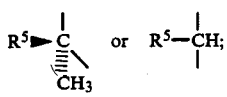

$R^5$ is H or OH:
$R^6$ is hydrogen or methyl; and a, b, c, and d represent optional double bonds, especially where b and d represent double bonds or a, b, c, and d are all single bonds.

U.S. Pat. No. 4,517,373 discloses semi-synthetic hydroxy containing compounds represented by the above general formula wherein $R^4$ is

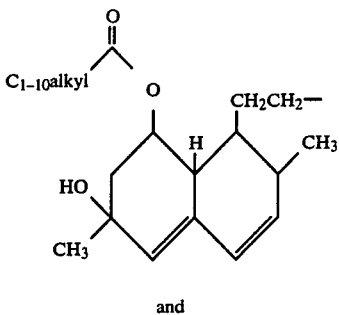

U.S. Pat. No. 4,346,227 and U.S. Pat. No. 4,448,979 also disclose semi-synthetic hydroxy-containing compounds represented by the above general formula wherein $R^4$ is

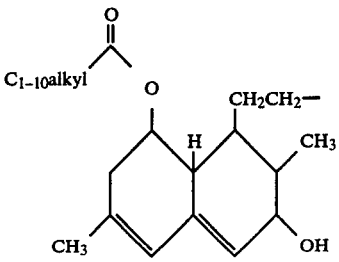

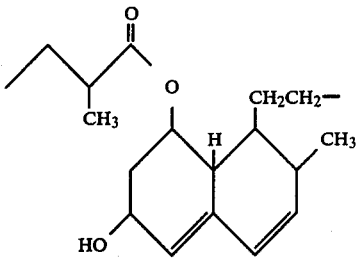

and

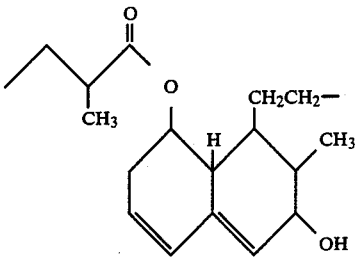

SUMMARY OF THE INVENTION

This invention relates to novel compounds which are HMG-CoA reductase inhibitors and are useful as antihypercholesterolemic agents. Specifically, the compounds of this invention are metabolites of mevinolin which possess a 2,3,5,6,7,8-hexahydronapthyl moiety and a 3-hydroxy group. Additionally, pharmaceutical compositions of these novel compounds, as a sole therapeutically active ingredient, and in combination with bile acid sequestrants are disclosed.

DETAILTED DESCRIPTION OF THE INVENTION

The specific HMG-CoA reductase inhibitors of this invention are the compounds represented by the following general structural formulae (I) and (II):

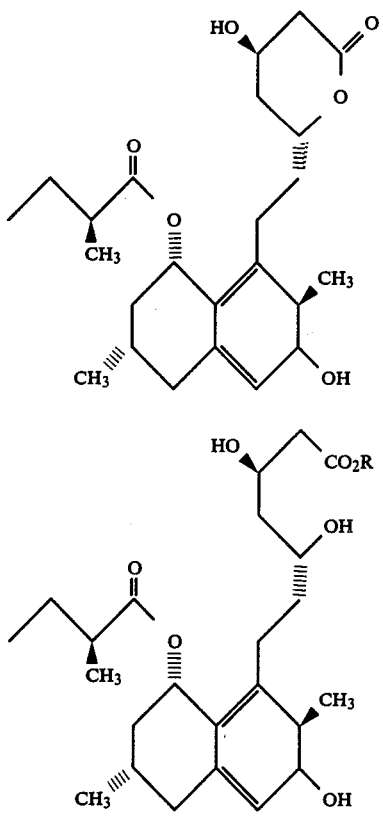

wherein R is hydrogen, $C_{1-5}$ alkyl, $C_{1-5}$ alkyl substituted with a member of the group consisting of phenyl, dimethylamino, or acetylamino
and pharmaceutically acceptable salts of the compound (II) in which R is hydrogen.

One embodiment of this invention is the compound of the formulae (I) and (II) wherein R is hydrogen.

Illustrative of this embodiment is 6(R)-[2-[8(S)-(2-methylbutyryloxy)-2(S), 6(R)-dimethyl-3-hydroxy-2,3,5,6,7,8-hexahydronaphthyl-1-]ethyl]-4(R)-hydroxy-3,4,5,6-tetrahydro-2H-pyran-2-one.

Another embodiment of this invention is the class of compounds of the formula (II) wherein R is $C_{1-5}$ alkyl and pharmaceutically acceptable salts of the compounds of the formula (II) wherein R is hydrogen.

The pharmaceutically acceptable salts of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compound of the formula (I) is conveniently prepared from mevinolin by the incubation with rat liver microsomes.

The compounds of the formula (II) wherein R is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein R is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol described is *J. Med. Chem.*, 1985, 28, page 347.

The compound of the formula (II) wherein R is hydrogen as the potassium salt exhibited an $IC_{50}$ of 0.24 $\mu$g/ml in the above reference protocol.

Included within the scope of this invention is the method of treating arteriosclerosis, familal hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-(2-Methylbutyryloxy)-2(S), 6(R)-dimethyl-3-hydroxy-2,3,5,6,7,8-hexahydronaphthyl-1-]ethyl]-4(R)-hydroxy-3,4,5,6-tetrahydro-2H-pyran-2-one

[$^{14}$C]Mevinolin (3.4 mg (8.4 umoles), 0.23 mCi/mmole) was incubated with 10.2 mg of rat liver microsomes for 60 minutes at 37° C. Also present in the incubation were 100 mM K phosphate buffer, pH 7.5, 1.0 mM triphosphopyridine nucleotide, sodium salt (NADP), 10 mM glucose-6-phosphate, 7 units of glucose-6-phosphate dehydrogenase and water to make 10.0 ml. The rat liver microsomes were prepared from male S.D. rats 150–200 gm in weight. The animals were injected i.p. with 80 mg/kg of Na phenobarbital once daily for 4 days, killed on day 5, and microsomes prepared from the livers by the method of Lu and Levin [Biochem. Biophys. Res. Commun. (1972) 46: 1334].

The reaction was stopped by the addition of 20 ml of ethanol followed by centrifugation and separation of the clear supernatant. The supernatant was concentrated to dryness in vacuo, and the residue extracted three times with 3 ml of ethyl acetate and twice with 3 ml of acetonitrile. The combined organic phases were concentrated to dryness in vacuo and the residue dissolved in acetonitrile (200 μl). The desired product was purified by HPLC on a 0.46×25 cm ultra sphere-ODS column eluted with 35 percent acetonitrile in 0.5 mM acetic acid for 3 minutes followed by a gradient of 35–80 percent acetonitrile over 12 minutes. The desired product was collected from the fractions with a retention time of 3.5 to 4.5 minutes. Mass spectrometry and nuclear magnetic resonance spectroscopy confirm the structure NMR (acetone-$d_6$): 3.80 δ (1H, t, 4: assigned to H-3), 5.76 δ (1H, dd, 4, 2: assigned to H-4). Double irradiation established protons are on adjacent carbons. Characteristic mevinolin vinyl proton resonances at 6.01, d, H-4, 5.80 dd, H-3 and 5.54 t, H-5 are absent.

EXAMPLE 2

As a specific embodiment of a composition of this invention, 20 mg of the compound of Example 1 is formulated with sufficient finely divided lactose to provide a total amount of 580 to 590 mg to fill a size 0 hard gelatin capsule.

What is claimed is:

1. A substantially pure compound which is 6(R)-[2-[8(S)-(2-methylbutyryloxy)-2(S),6(R)-dimethyl-3-hydroxy-2,3,5,6,7,8-hexahydronapthyl-1]ethyl]-4(R)-hydroxy-3,4,5,6-tetrahydro-2H-pyran-2-one.

2. A hypocholesterolemic, hypolipidemic pharmaceutical composition comprising a nontoxic therapeutically effective amount of a compound of claim 1 and a pharmaceutically acceptable carrier.

3. A method of inhibiting cholesterol biosynthesis comprising the administration to a subject in need of such treatment a nontoxic therapeutically effective amount of a compound of claim 1.

* * * * *